United States Patent
Raidel et al.

(10) Patent No.: US 7,189,448 B2
(45) Date of Patent: Mar. 13, 2007

(54) APPARATUS AND PROCESS FOR PRODUCING A CORRUGATED WEB AND AN ABSORBENT ARTICLE COMPRISING A CORRUGATED WEB

(75) Inventors: Maria Raidel, Nuremberg (DE); Jan Ullman, Nuremberg (DE); Franz Aschenbrenner, Kastl (DE)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 248 days.

(21) Appl. No.: 10/406,350

(22) Filed: Apr. 3, 2003

(65) Prior Publication Data

US 2003/0224146 A1 Dec. 4, 2003

Related U.S. Application Data

(60) Division of application No. 09/483,680, filed on Jan. 14, 2000, now Pat. No. 6,548,147, which is a continuation of application No. 08/765,423, filed on Jun. 23, 1997, now Pat. No. 6,171,682, which is a continuation of application No. PCT/EP95/02550, filed on Jun. 30, 1995.

(30) Foreign Application Priority Data

Jun. 30, 1994 (DE) .............................. P4422956.9

(51) Int. Cl.
*B32B 3/28* (2006.01)

(52) U.S. Cl. ..................... 428/167; 428/182; 428/183; 428/184; 428/185; 604/385.01; 604/385.02

(58) Field of Classification Search ........ 428/182–185, 428/167; 604/385.01, 385.02; 442/401, 442/394, 382
See application file for complete search history.

(56) References Cited

U.S. PATENT DOCUMENTS

| 2,158,087 A | 5/1939 | Rowe et al. | 154/30 |
| 2,494,431 A | 1/1950 | Eckstein | 154/30 |
| 2,960,145 A | 11/1960 | Ruegenberg | 154/30 |

(Continued)

FOREIGN PATENT DOCUMENTS

EP 0 062 495 B1 10/1982

(Continued)

OTHER PUBLICATIONS

Derwent World Patent Database abstract of DE 2945395: Description of S. Wakasono, "Pleat-Sewing Machine Fabric Guide." May 21, 1981.

(Continued)

*Primary Examiner*—Elizabeth M. Cole
(74) *Attorney, Agent, or Firm*—Dority & Manning P.A.

(57) ABSTRACT

Absorbent article comprising a liquid-impermeable cover sheet, a liquid-permeable cover sheet, and an absorbent body between the liquid-impermeable cover sheet and the liquid-permeable cover sheet. Any one or all of the liquid-impermeable cover sheet, the liquid-permeable cover sheet, or the absorbent body can be made of a corrugated web which is corrugated from a sheet material which, in the process of being corrugated, is drawn in, and optionally elongated in a direction transverse to the corrugations, alternatively drawn-in along a direction transverse to a length of the web. The corrugated web can comprise corrugations of differing heights (H1).

28 Claims, 10 Drawing Sheets

U.S. PATENT DOCUMENTS

| | | | | |
|---|---|---|---|---|
| 3,494,362 | A | * | 2/1970 | Burgeni .................. 604/374 |
| 3,525,337 | A | | 8/1970 | Simons et al. ............ 128/290 |
| 3,692,615 | A | | 9/1972 | Ohmori .................. 425/370 |
| 4,111,733 | A | | 9/1978 | Periers .................. 156/204 |
| 4,144,618 | A | | 3/1979 | Campo et al. ............ 19/161.1 |
| 4,170,347 | A | | 10/1979 | Lewis .................... 270/94 |
| 4,252,591 | A | | 2/1981 | Rosenberg ............... 156/203 |
| 4,266,700 | A | | 5/1981 | Wakasono ................ 223/34 |
| 4,389,211 | A | * | 6/1983 | Lenaghan ................ 604/383 |
| 4,578,070 | A | | 3/1986 | Holtman .................. 604/378 |
| 4,848,572 | A | | 7/1989 | Herrera .................. 206/440 |
| 5,185,052 | A | | 2/1993 | Chappell et al. .......... 156/462 |
| 5,906,879 | A | | 5/1999 | Huntoon et al. .......... 428/136 |

FOREIGN PATENT DOCUMENTS

| | | |
|---|---|---|
| EP | 0 137 644 B1 | 4/1985 |
| FR | 854979 | 4/1940 |
| FR | 1468101 | 2/1967 |
| WO | WO 9111161 A1 * | 8/1991 |
| WO | WO 9507674 A2 * | 3/1995 |
| WO | WO 96/00625 A2 | 1/1996 |

OTHER PUBLICATIONS

Derwent World Patent Database abstract of DE 2827495: Description of E.A. Campo, "Strip Material Transport Mechanism." Jan. 11, 1979.

Derwent World Patent Database abstract of DE 2011802: Description of H. Ohmori, "Paper Web Corrugating Machine." Mar. 19, 1981.

* cited by examiner

APPARATUS AND PROCESS FOR PRODUCING A CORRUGATED WEB AND AN ABSORBENT ARTICLE COMPRISING A CORRUGATED WEB

This application is a division of 09/483,680, filed Jan. 14, 2000, now U.S. Pat. No. 6,548,147 which is a continuation of 08/765,423, filed Jun. 23, 1997, now U.S. Pat. No. 6,171,682 which is a continuation of PCT EP95/02550, filed Jun. 30, 1995.

The invention relates to apparatus and process for continuously producing a web from a thin sheet material which is corrugated at least in partial sections thereof and elastic at least in transverse direction. Moreover, the invention relates to an absorbent product comprising a corrugated web.

From examined German patent application DE 2011802 B2 laid open for public inspection an apparatus is known which deals with the corrugation of a paper web. Due to the material properties of the paper to be processed, the shape of the guide bed of the known apparatus must be geometrically very complex and physically curved, which requires a high expenditure in production engineering and is thus disadvantageous.

From German patent DE 2945395 C2 a forming plate for a folding device of a cording machine is known consisting of a base plate and a plurality of folding ribs on the surface thereof, which ribs comprise parallel extending portions projecting beyond one edge of the base plate and portions extending radially or fan-shaped on the base plate. The folding ribs are separate blades which are releasably attached to the base plate and disposed in grooves formed in the base plate, each of which exhibits in a partial section a recess into which holding brackets engage which project from the lower edge of the blades. The known device does not enable a stabilization of corrugations. The corrugations formed are much rather pressed flat and fixed by sewing in a tune shape on the initial web.

A further device for forming longitudinal folds in a continuous web is described in German patent DE 3611134 C2. In this device, a very elastic paper which can be made almost plastically deformable by moistening, e.g., for cigarette filters, is slowly drawn into corrugations from the centre outwards between a large number of nested combing rollers. The embodiment shown of this very complex machine is only intended for forming corrugations in sections. Corrugations cannot be produced over the whole web due to the constant alternate web curvature.

Finally, German patent DE 2827495 C2 describes a device for transporting and combining a web of material in which the main aspect of the invention is the transportation of the web and simultaneous funnel-shaped tapering using a flow of air. It is not possible to obtain an exact corrugation of the folds with the known device.

The present invention is thus based on the object of providing an apparatus and process for producing corrugated webs and absorbent articles which avoid the drawbacks of the prior art. This object is solved according to the invention by the apparatus, the process, and the absorbent articles taught herein. Further advantageous embodiments, aspects and details of the invention are evident from the dependent claims, the description and the drawings.

The apparatus of the invention comprises a guide bed into which fan-shaped grooves are cut, the depths of said grooves increasing preferably linearly to produce a corrugated cross-section of the desired dimension, into which holding-down devices dip from the opposite side according to the available height. The corrugated webs produced by means of the apparatus of the invention may have the same corrugation height over the entire web width of different corrugation heights if the guide bed is configured accordingly. It is self-evident to the person skilled in the art that the guide bed may also comprise one groove only if the desired corrugated web shall exhibit corresponding properties. In this case, only one holding-down device is required as well. The holding-down devices are preferably rod-shaped and preferably freely shiftable perpendicular to the guide bed at the end facing the inlet end of the guide bed as well as at the end facing the outlet end of the guide bed. The holding-down devices can be supported at both ends or may have one free unguided or unsupported end. It is advantageous for the holding-down devices to be of certain elasticity. Spring steel is a suitable material for the holding-down devices. The holding-down devices may be guided in at least one guide face extending perpendicular to the guide bed. If, in addition, the holding-down devices press the web against the guide bed through force-exerting means with a predetermined load, this will permit a certain adjusting effect for the continuous web which compensates for differences in tension in the material due to the formation of the folds not always being geometrically accurate. The predetermined force exerted on the holding-down devices can also be applied by a biasing of the holding-down devices. This renders additional force exerting elements superfluous. Besides a round cross-section of the holding-down devices, which is particularly preferred, the holding-down devices may also have a triangular, rectangular, semicircular or trapezoidal trapezoidal cross-section.-

It is of particular advantage for the free ends of the holding-down devices to be bent substantially parallel to each other or provided with corresponding shoulders which are received in bores of at least one guide element positioned at the end face. Furthermore, with respect to the direction of movement of the web, it is advantageous for all holding-down devices to be received forward and rearward, respectively, of the surface portion of the guide bed which comprises the grooves. Preferably, the holding down devices are of round cross-section. The diameter may be, for example, from 0.1 to 5mm, preferably 1 to 3mm, in particular 2mm. The distance between the grooves may be, for example, from 1 to 5 to 10 mm, preferably 2 to 4 mm.

The force-exerting means may, for example be a pressure plate which acts between the ends of the holding-down devices on same. The pressure plate, may additionally be provided with at least one spring member. Weights, compressed air, vacuum or -magnets may also be used to exert a force- If magnets are used, permanent magnets as well as electromagnets are suitable which should be provided on the side of the guide bed opposite to the web to be formed. It is self-evident to the person skilled in the art that, when use is made of a magnet, the holding-down devices or an element acting on the holding-down devices, e.g., a contacting pressure plate, should exhibit ferromagnetic properties.

The corrugated webs of thin material produced by means of the apparatus of the invention or the process of the invention must be fixed after leaving the guide bed in order for the corrugations to remain permanently. One possibility to fix the corrugated web is to join it with a web material (backing web) or several web materials (backing webs). Another fixation possibility is to plastically deform the corrugated web permanently between stamping rollers. Furthermore, it is possible to fix the corrugation of the corrugated web in that a hardening agent is sprayed on. If a backing web is used to stabilize the corrugated web, the webs are preferably joined by a bonding agent, such as an adhesive. The joining, however, can also be effected by thermal treatment or ultrasonic welding.

According to a further embodiment, the guide-bed is provided, seen in cross-section, with different corrugation heights, the maximum corrugation height being usually formed in the center, the corrugation height decreasing towards the edges of the guide bed.

Furthermore, it is advantageous for the guide bed to be provided, seen transversely of the direction of movement of the material web, such that not all grooves start at the same height. It is particularly preferred for the grooves to start in the central portion of the guide bed, with grooves starting further downstream being arranged in the peripheral portions. Furthermore, it is desirable in certain embodiments for the guide bed to be so arranged as to be not provided with grooves over the entire width such that no grooves are provided in the central portion and/or the peripheral portions of the guide bed.

Finally, the apparatus of the invention may comprise a device with meshing rollers for stamping the produced corrugated web, said device with meshing rollers being provided downstream of the guide bed.

The corrugated web produced with the process of the invention and the apparatus of the invention can advantageously be used as component of an absorbent article for absorbing body fluids, such as a diaper, sanitary napkin or incontinence pads. Such an absorbent article usually comprises a liquid-impermeable cover sheet disposed away from the body in use, a liquid-permeable cover sheet disposed towards the body in use and an absorbent body disposed between said liquid-permeable and said liquid-impermeable cover sheet. The absorbent article of the invention is distinguished in that the liquid-permeable cover sheet and/or the absorbent body comprises at least in partial sections thereof corrugations ("pleatings"). To this end, webs can be used which have been laid in folds by means of the process of the invention or the apparatus of the invention. The webs produced according to the invention are advantageous as compared to corrugated webs conventionally produced by means of stamping rollers in that they are of superior wearing comfort and improved absorbing capacity, because the treated material is practically not compacted in the forming process.

The invention is described in more detail below with reference to the attached drawings, wherein.

Figure 1:
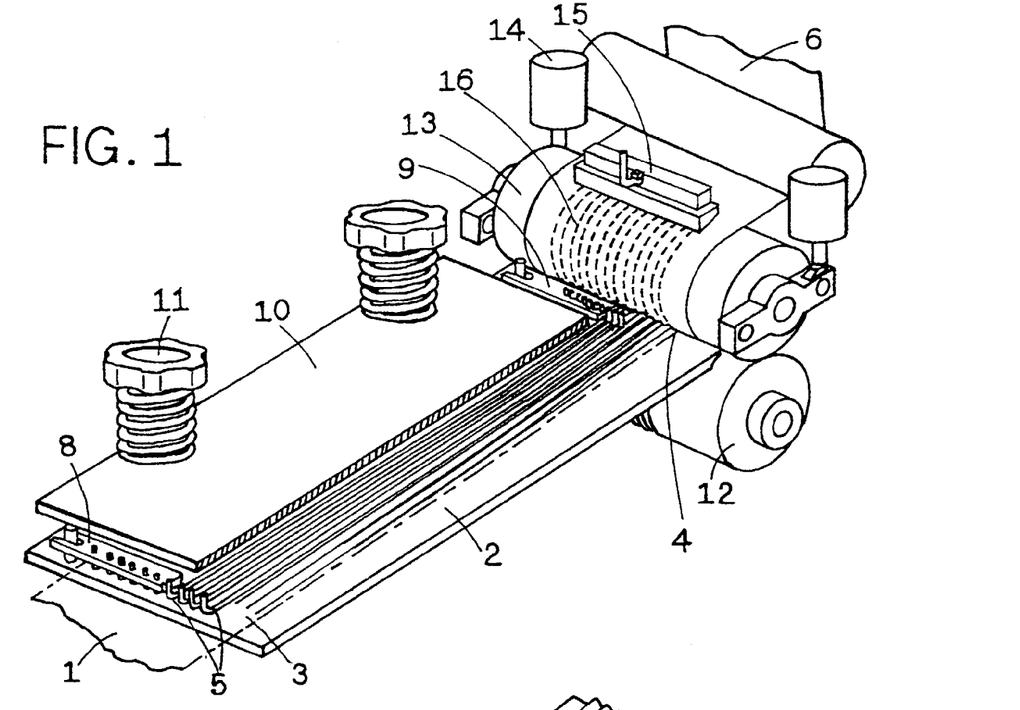
FIG. 1 is a perspective, partly cut-open view of a machine for producing a corrugated web from highly elastic material which is bonded to a backing web.

According to FIG. 1, the web 1 to be corrugated enters the corrugating device at the front edge 3 of the guide bed 2, is pressed into the guide bed by the rod-shaped holding-down devices 5 and leaves the guide bed in corrugated form at the outlet end 4. The holding-down devices are held in a front spacer 8 and a back spacer 9 so as to keep them at a constant distance apart from one another, and in the embodiment of FIG. 1 they are pressed down with a defined force by means of a spring-loaded pressure plate 10 adjustable via set screws 11. The holding-down devices are supported to be freely shiftable in the direction of the guide bed.

Figure 10:
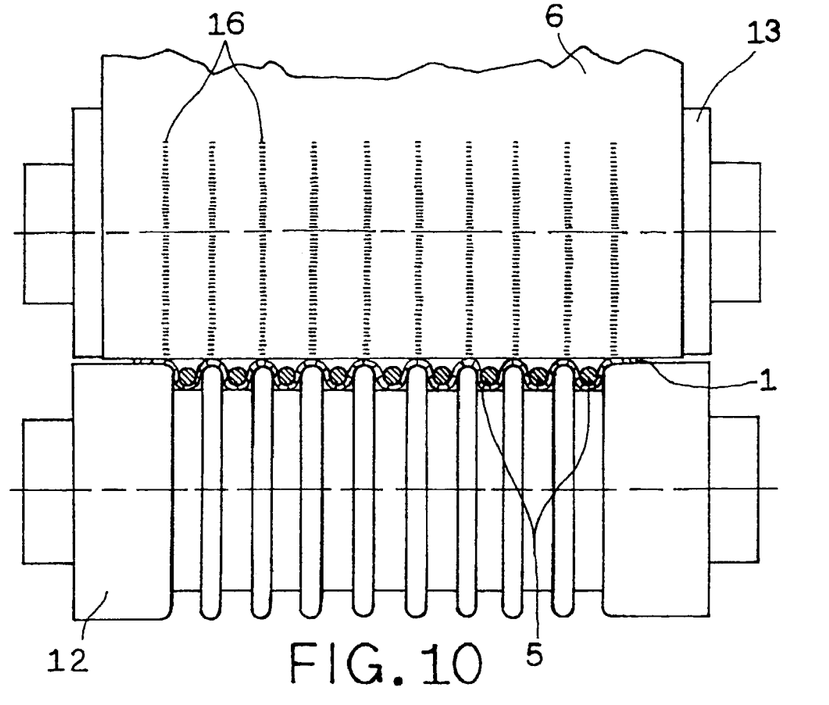
FIG. 10 is a view of the two rollers of the bonding station with the holding-down devices engaging into the corrugated roller and the application of adhesive in lines.

The corrugated web is joined with the backing web 6 directly after leaving the guide path 2 which is effected by means of a smooth roller 13 and a roller 12 with profiled cross-section as shown in the view of FIG. 10. The pressure force required for the subsequent bonding of the sheets is provided here by means of two pneumatic cylinders via levers.

In order to join the backing web with the corrugated web, a solution is shown here in which use is made of an adhesive applied in lines 16 by means of a multiple nozzle 15 for adhesive application. Due to the specific shape and attachment of the rod-shaped holding-down devices, the ends of which extend into the profiled roller 12, as is also evident from FIG. 10, the corrugations formed in the web are prevented from springing back prior to bonding.

Figure 2:
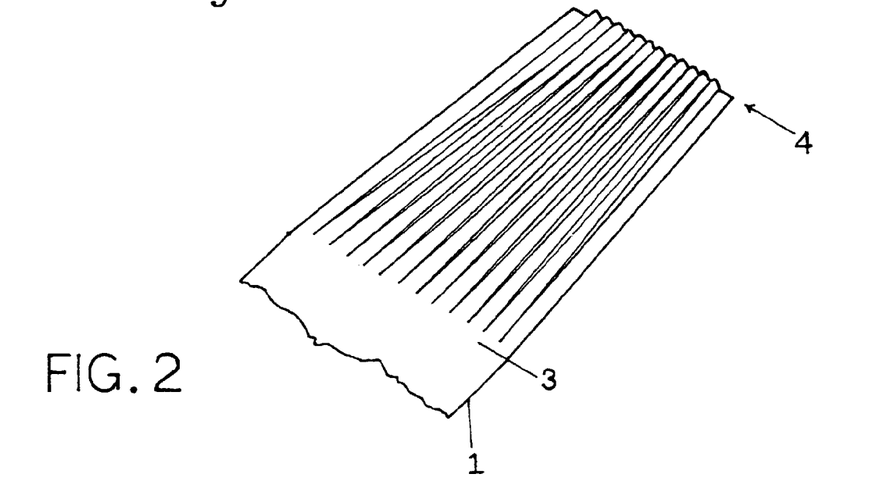
FIG. 2 is a perspective plan view of the corrugated web which also represents the shape of the guide bed in a preferred embodiment.
Figure 3:
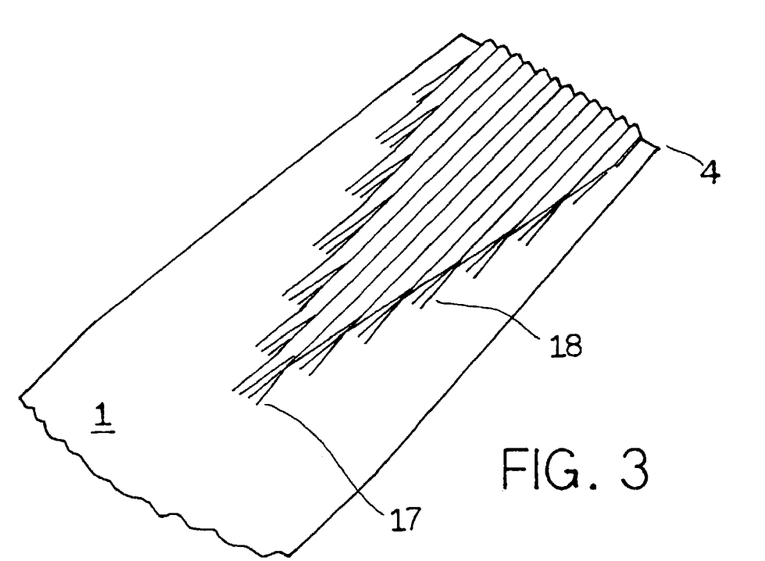
FIG. 3 is a perspective view of an alternative corrugation configuration starting in the centre.

The corrugated web 3 in FIG. 2 corresponds essentially to the planar guide bed. A linear increase in the corrugations is evident which permits simple manufacture of the forming device. To reduce local tensions in a less elastic material, it is advantageous for the guide bed to be formed as shown in FIG. 3, with the corrugation formation starting in the centre of the web and being gradually followed by corrugations further towards the edge. However, in such a configuration the installation of the holding-down devices involves an increased expenditure in production engineering, since they must form the full corrugation height over paths of different length and have different inclinations relative to the guide bed.

Figure 4:
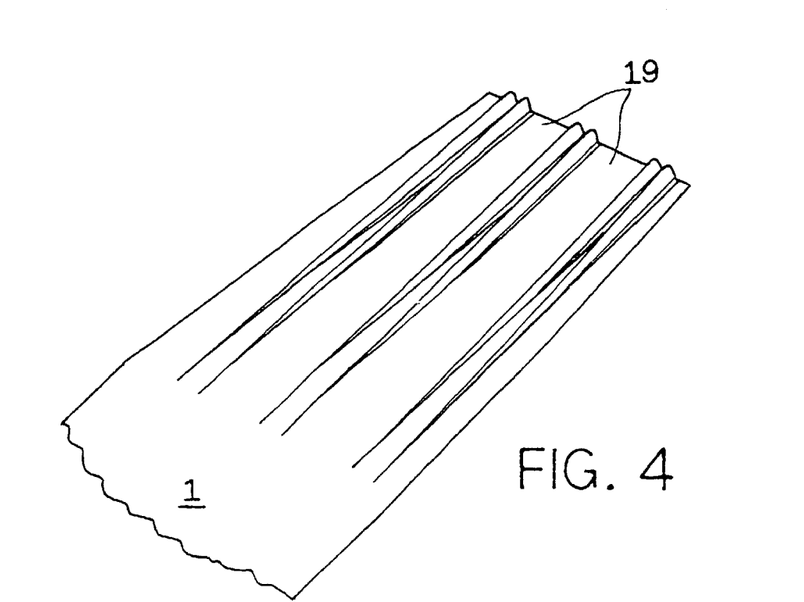
FIG. 4 is a perspective plan view of a web or guide bed with partial corrugations only.

For webs which, according to the invention, are not to be corrugated over the entire width, the shape of the guide bed may be as shown in FIG. 4 with only a few corrugations with planar guide bed sections 19 therebetween. In the extreme case, the guide bed may comprise one groove only, as already mentioned above.

Figure 5A:
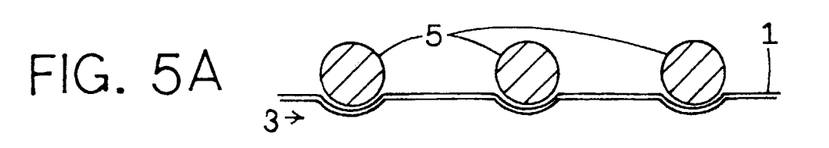
FIGS. 5a, 5b, and 5c are cross-sections through the guide bed at the beginning, in the centre and at the end with schematic representation of the drawn-in web.
Figure 5B:
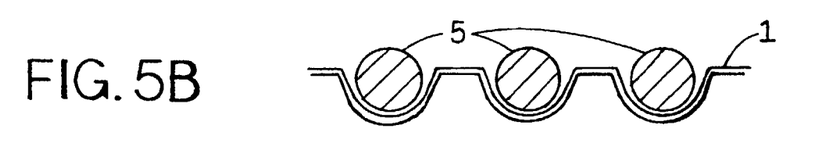
Figure 5C:
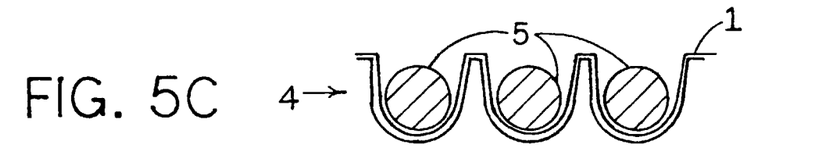

The configuration of the guide bed and the holding-down devices can result in a draw-in behavior which are not uniform over the entire length of the corrugation formation path as is shown schematically in FIGS. 5a, 5b, and 5c. By means of the a calculation program, the draw-in factor can be determined and optimized for the web to be corrugated at any point of the guide bed. According to the solution provided by the invention, the ideal value is achieved at the beginning of the corrugation configuration, as shown in FIG. 5a, and at the end, as shown in FIG. 5c, whereas only about 92% of the material is drawn-in at the centre of the guide bed, as shown in FIG. 5b, which is, however, compensated for by the elasticity and low flexural strength of the web.

Depending on the intended use, most various corrugation shapes can be theoretically produced as shown in FIGS. 6a, 6b, 6c, and 6d. However, the cornered corrugations according to FIG. 6a and FIG. 6b require a chemical and physical treatment, for example, by spraying with a hardening agent, thermal hardening or strong plastic deformation by stamping, in order to maintain the cross-section shown. The draw-in values differ between 1.41 for 45 ° C. triangular corrugations and 1.32 for the trapezoidal shape with ⅓ straight section and a value 2 to 600 ° C. inclination of the corrugation or 1.66 for the trapezoid.

Figure 6A:
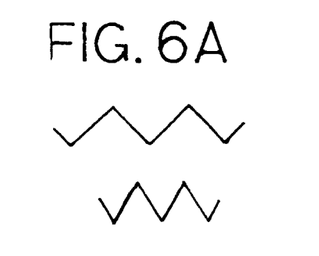
FIGS. 6a, 6b, 6c, and 6d show different theoretically possible shapes of the corrugated web with different draw-in factors.
Figure 6B:
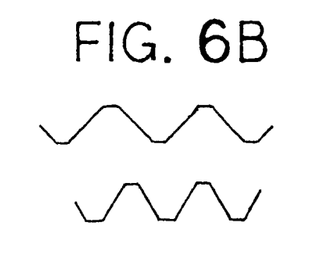
Figure 6C:
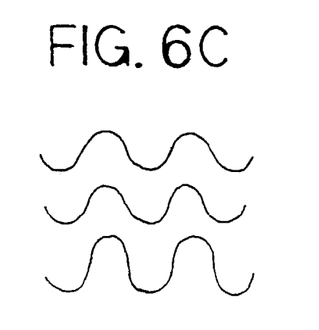
Figure 6D:
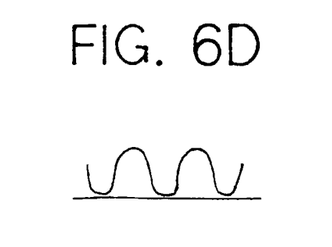

For the preferred embodiment FIG. 6c with semi-circles and straight sections of more or less length, the material draw-in is between 1.45 for short straight sections with 50° C. inclination sections. The two contiguous semi-circles are a special case. The draw-in factor in this case is exactly $\pi/2$, i.e., 1.57. This corrugation shape is also advantageous as far as the balance of internal tensions and the stability to external forces is concerned, without additional stabilizing measures being applied. When being bonded to a backing web, the corrugations will be automatically flattened to a certain extent—depending on the bonding process—so that the actually produced corrugation cross-section assumes the shape FIG. 6d.

Figure 7:
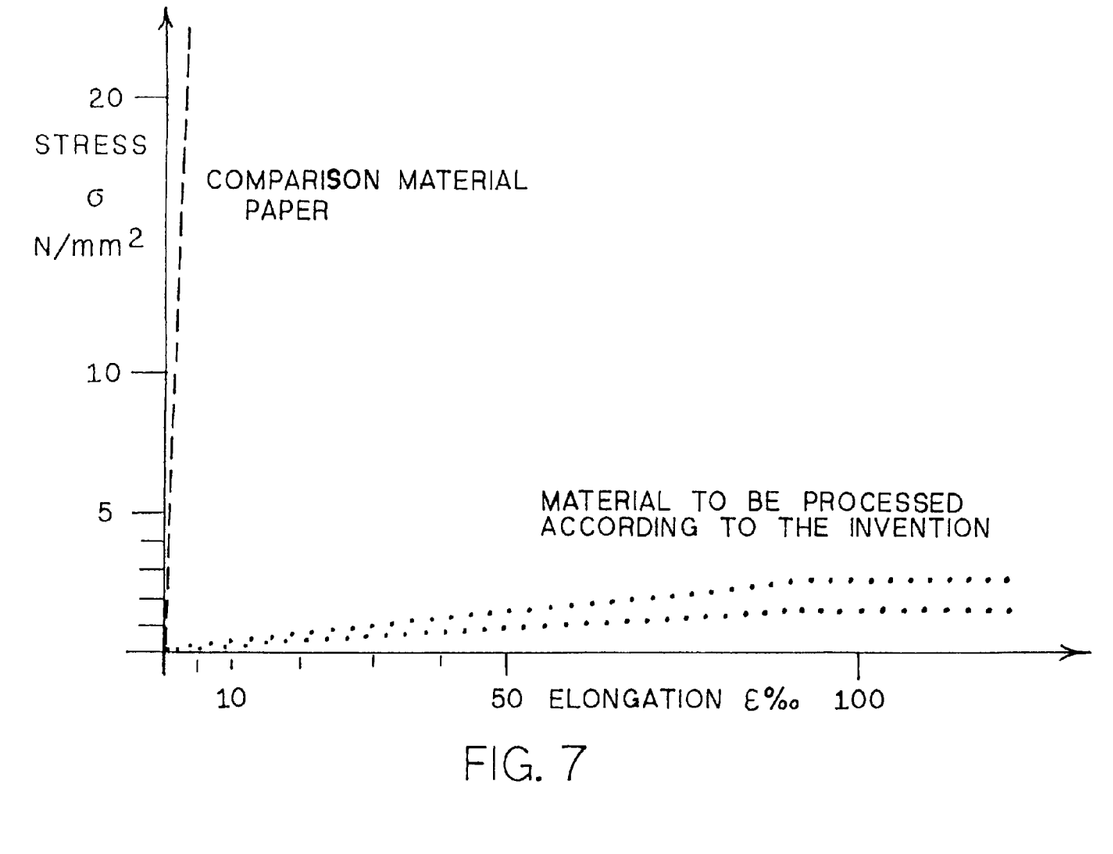
FIG. 7 represents material-technical considerations for webs to be preferably processed.

In order to be capable of being passed through the apparatus of the invention, the web to be processed should have certain physical properties: low flexural strength rigidity and high elasticity. These requirements are, for example, fulfilled by low-density fibrous materials and plastic foils. FIG. 7 shows a stress-strain curve for different materials. In contrast to paper, which requires little deformability and high strength in production, such materials exhibit a certain deformability and a yield limit which is mostly not defined exactly and high breaking elongation. Preferably, the processed material webs are elastic at least in transverse direction.

For the formation of corrugations, the web is calculated to require at the end of the forming process a distance in transverse direction approximately 8% greater than in the middle of the process, which every material examined so far withstood without problems, because this results at best in a minimal permanent deformation which is not even undesired in the present case of the application.

Accordingly, the machine with a guide bed of simple design for producing corrugations in thin webs is in particular suited for all materials which can bear about 10% elongation or more without breaking, in a direction of extension transverse to the direction of extension of the grooves, and corresponding ridges, of the corrugation.

The following Table 1 shows a few examples of materials or material combinations which can be processed with the apparatus of the invention and by means of the process of the invention for producing corrugated webs. The webs produced are also referred to as "pleated" webs and, accordingly, the material used for this purpose is also referred to as "pleatable" material.

TABLE 1

| Materials | Dimensions | Carded nonwoven | Spunbonded nonwoven | Laminate: Carded nonwoven/ perforated foil | Laminate: Spunbonded/ perforated foil |
|---|---|---|---|---|---|
| Basis weight | g/m² | 18 | 16 | 43 | 42 |
| Thickness | mm | 0.18 | 0.13 | 0.92 | 0.50 |
| Strength, dry | | | | | |
| longitudinal | N/50 mm | 40 | 30 | 55 | 13 |
| transverse | N/50 mm | 18 | 20 | 19 | 6 |
| elongation, dry | | | | | |
| longitudinal | % | 50 | 50 | 35 | 34 |
| transverse | % | 90 | 60 | 150 | 78 |
| Friction, dry | | | | | |
| Inner side (foil) | µD | 0.65 | 0.33 | 0.41 | 0.30 |
| Outer side (nonwoven) | µD | 0.65 | 0.33 | 0.41 | 0.93 |

In order to provide uniform corrugation configuration with the apparatus of the invention it is advantageous that a defined force acts on the web which is exerted by the holding-down devices. This may be accomplished by means of weights, spring force (see FIG. 1) or also adjustable during operation by means of pneumatic or hydraulic cylinders 20 in accordance with FIG. 8, a pneumatic cylinder being preferred due to the low forces required and less leakage. For reasons of compactness, this cylinder may be installed longitudinally, for example, and act on the pressing plate 10 via knee levers 21. According to theoretical examinations and practical test results, depending on the material treated in each case, a linear load of from 0.04 to 0.06 Ncm$^{-1}$ has proved favourable for web speeds of up to 150 m/min. The total contact force thus reaches about 20 N at a guide bed length of 300 mm. If the basis weight and/or the flexural strength of the material is changed, a load of, for example, 0.01 to 0.1 Ncm$^{-1}$, preferably 0.02 to 0.08 Ncm$^{-1}$ is suitable. Apart from the adjustability of the holding-down forces, the use of pneumatic cylinders is also advantageous in that the device can be pneumatically lifted and relieved for entering the web. Web speeds of up to 250 m/min are obtainable with suitable materials.

Figure 8:
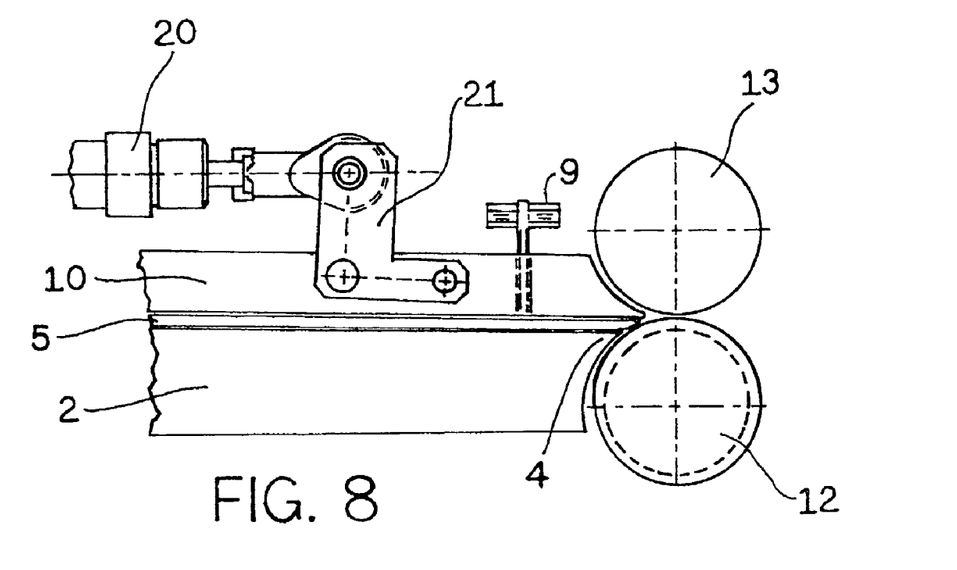
FIG. 8 is a side view of the guide bed end with a bonding device as well as the fixation of a pressing means for the holding-down devices by means of pneumatic cylinders and knee lever.

FIG. 8 is a side view of the holding-down rods 5 which extend into the profiled roller 12 together with the rearward support 9 which is adjustable by means of clamping screws.

Figure 9:
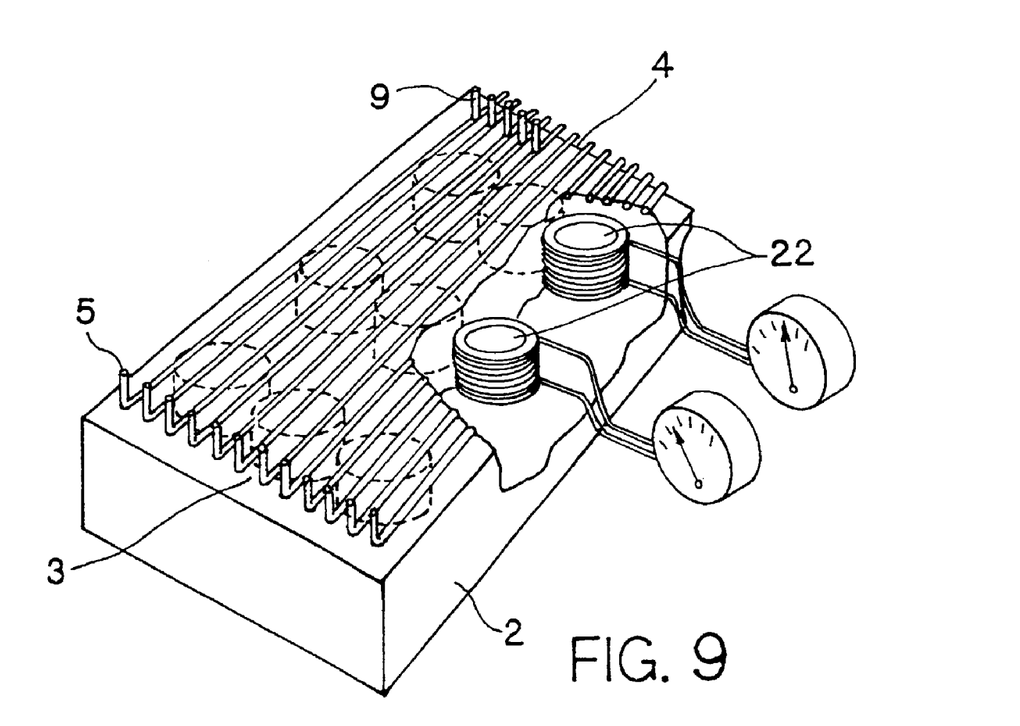
FIG. 9 is a partially cut-open perspective view of the guide bed and the holding-down devices to which variable forces can be applied sectionwise by means of separately activatable electromagnets.

In order to obtain an even more individual force distribution in the holding-down devices, electromagnets 22 may be accommodated in the guide bed of the apparatus of the invention as is shown in the preferred embodiment of FIG. 9, said electromagnets being activated, as required, either in groups or individually, the formation of corrugations being thus influenced with particular sensitivity. The ferromagnetic holding-down rods 5 are attracted by the electromagnets with up to 0.1 Nmm$^{-2}$, i.e., with a rod width of 2 mm, either a very low current or a correspondingly distributed small number of individual magnets suffices to produce the required contact pressure. This solution involves the advantage that, regardless of a possibly different degree of wear of the holding-down rods, a uniform corrugation formation is nevertheless enabled without readjustments being required.

Due to the instability of the processed material, the corrugations formed would spring back to the initial planar condition after leaving the forming apparatus if no additional measures were applied, e.g., joining with a backing web, thermoplastic modification or fixation by means of a sprayed-on hardening agent.

If a backing web is used for stabilization, it can be made from the same material as the corrugated web or of a different material. The joining with a backing web is preferably effected, as shown in FIGS. 1 and 10, by bonding a planar web 6 with the peaks (maxima and minima) of the corrugated web 1 formed. In this procedure, the corrugations are forcibly held between a roller 12 provided with grooves, corresponding to the distance of the holding-down devices 5, and the rod ends of the holding-down devices, while a roller pressed from above, e.g., via the pneumatic cylinders, supplies the second web 6 to which adhesive 16 is applied in lines in the area of the corrugation peaks by means of a multiple nozzle.

The joining of the corrugated web with the backing web according to FIG. 1 by the application of adhesive 16 in lines is only one of the possibilities suitable for this purpose. The use of wheel or screen printing devices as adhesive applicators is conceivable.

As the apparatus of the invention can preferably be used for the processing of webs of synthetic foils or nonwoven webs, the corrugated web formed can be welded to the backing web by introducing thermal energy, e.g., via the corrugated transport roller 12.

A similar bonding effect is obtained by pressing the webs together in the valleys of the upper corrugated web, i.e., using an ultrasonic press shoe or a press roller.

Figure 11:
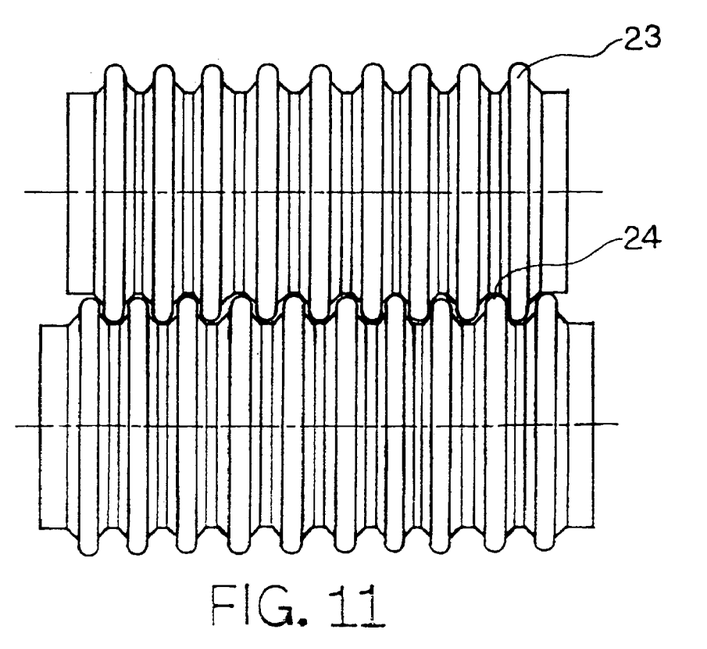
FIG. 11 is a schematic view of stamping rollers disposed after the guide bed which deform the corrugated web at the corrugation peaks by pressing for the purpose of fixation.

To fix the shame of the corrugations also without an additional backing web, the corrugated web can be plastically deformed at the peaks 24 of the corrugations between stamping rollers 23 having a corrugated cross-section, preferably in accordance with FIG. 11. This effect can also be obtained or increased by thermal or chemical-physical action such as spraying with a hardening agent.

Figure 12:
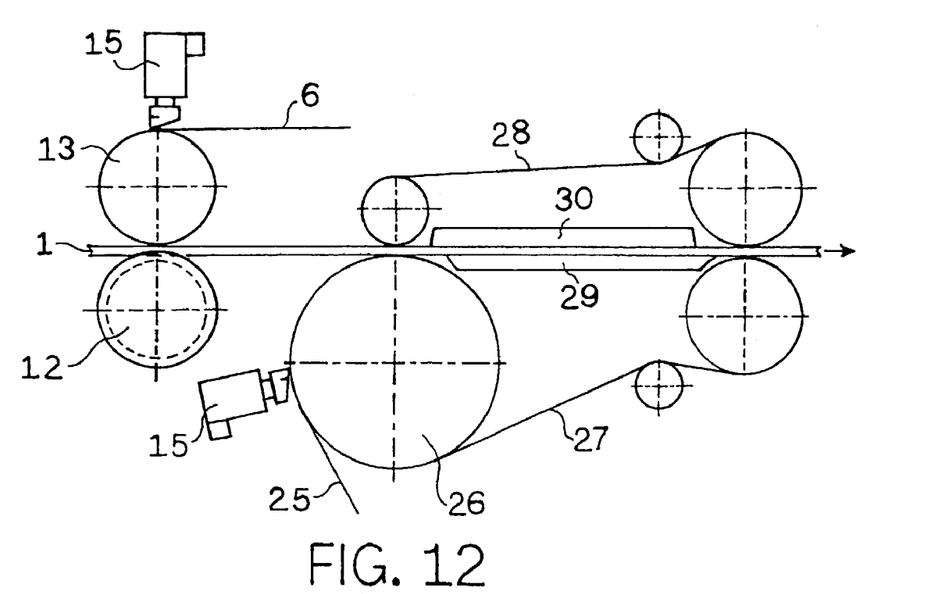
FIG. 12 is a schematic view showing the application of a second web with the following pressing station for fixing the adhesive bond.

A further advantageous embodiment of the invention consists in that, as shown in FIG. 12, the side of the corrugated web opposite to the backing web 6 is also bonded to a further material web 25. This material web 25 is also referred to as cover web. To this end, for example, this web can be fed by a roller of larger diameter 26 and a belt system 27, with adhesive being applied in lines by an application device 15. In an advantageous embodiment, bonding to the corrugated web 1 can be achieved by a second belt system 28 and a pressure device 30, which evenly distributes the contact pressure, the support 29 acting against the contact pressure.

Figure 13:
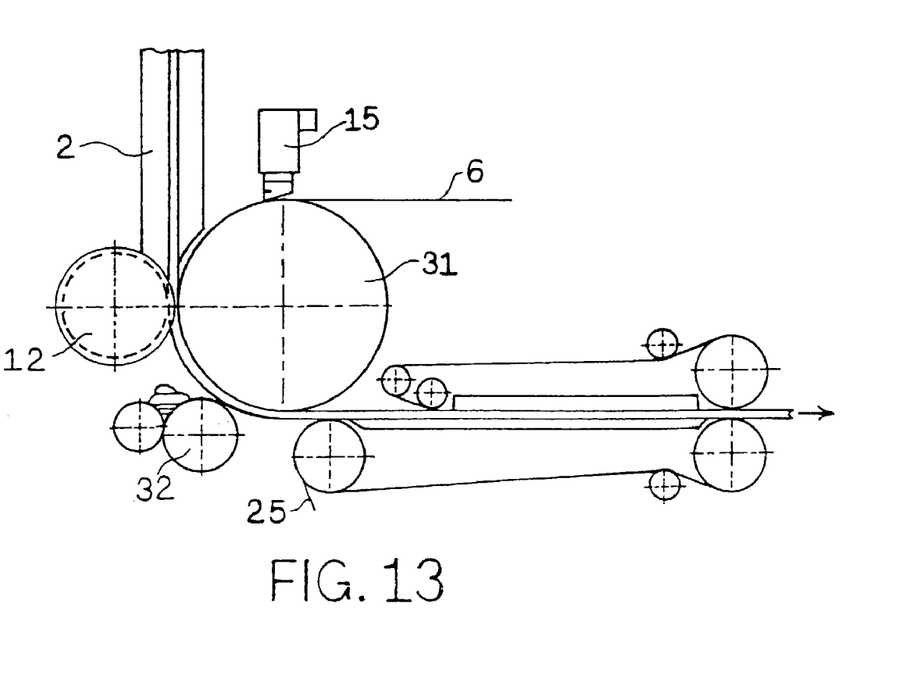
FIG. 13 is a schematic view of a further preferred embodiment for bonding the second web.

According to FIG. 13, the corrugated web leaving the guide bed 2 is pressed by a corrugated roller 12 against a smooth roller 31 of larger diameter and bonded to the backing web 6, to which, for example, adhesive has been previously applied in lines by means of a suitable device 15.

The curvature of the roller 31 is selected such that the corrugated web is only slightly elastically deformed and returns to its original cross-section after leaving the roller. Adhesive can be applied to the peaks of the corrugations in one area of the roller 31 using a basically known adhesive device 32. The joint is strengthened by a subsequent pressure section, as shown in FIG. 12, with a controlled contact pressure being applied.

Furthermore, the invention relates to an absorbent article suitable for absorbing body fluids. Such articles are, for example, articles for feminine care, like sanitary napkins, as well as diapers, incontinence pads and the like.

Said hygienic articles are known in most various forms. They all have in common a backside liquid-impermeable cover sheet, a frontside liquid-permeable cover sheet and an absorbent body between said two sheets.

The backside cover sheet is usually made from a thin polyethylene foil. Nonwovens are mostly used for the frontside liquid-permeable cover sheet. The use of perforated foils is also known.

The absorbent body usually consists of wood pulp fluff or an air-laid fibrous web, a so-called "air-laid material".

Apart from the basic absorbent capacity of the absorbent body, the properties of the frontside cover sheet, i.e., the body side layer, in terms of product engineering, such as tactile softness, rate of absorbency of body fluids, the distribution of the latter in the sanitary article and the rewetting properties are decisive. The nonwovens usually used for the bodyside cover sheet are largely comparable as far as the aforementioned properties are concerned.

Due to the frontside cover sheet being folded according to the invention, a surface effect is achieved which can best be described by the term "pleating".

The folds provide longitudinal channels on the surface of the sanitary article to improve the liquid distribution in longitudinal direction and at the same time barriers against liquid expansion in transverse direction. This results in a considerable improvement of the leak-proofness of the sanitary article.

Furthermore, the folds cause over considerable cover sheet portions a space to be formed between the latter and the absorbent body beneath which enhances the absorption and penetration of the body liquid into the absorbent body; at the same time the rewetting properties are improved. Moreover, the visual appearance after the application of, e.g, menstrual fluid, is improved because the projecting folded areas are not in contact with the liquid-soaked absorbent body. Not least, the resiliency of the folds influences the softness of the bodyside surface of the sanitary article, which improves the wear comfort and natural grip.

Such an effect—in terms of liquid distribution—can also be achieved with part of the absorbent body being provided in pleated form, or, in combination with a pleated cover sheet, even improved. Suitable materials for the pleated absorbent body are hydrophilic nonwovens, such as hydrophilic carded nonwovens or hydrophilic spunbonded nonwovens having basis weights of from 6 to 80 $g/m^2$, in particular 10 to 30 $g/m^2$, air laid fiber web and laminates.

Hydrophobic nonwovens, such as hydrophobic carded nonwovens and hydrophobic spunbonded nonwovens can be used for the pleated cover sheet. The basis weight of such materials is again in the range of from 5 to 6, to 30 to 80 $g/m^2$, in particular 10 to 20 $g/m^2$.

If, according to a preferred embodiment, the valley portions of the folds disposed towards the absorbent body are fixed on the absorbent body or a backing sheet disposed between the latter and the frontside cover sheet, the folds are so stabilized that the positive effects produced by them is maintained even after storage in pressed condition or prolonged periods of wear.

The valley portions of the contiguous folds can be fixed in that they are adhered (adhesive strip) or welded to the absorbent body or the backing sheet over a width (valley width F) of preferably 0.2 to 10 mm.

Thereby, the backing sheet can improve the functional properties of the folds, for example, as regards liquid transfer and rewetting.

The valley portions of two adjoining folds can be affixed at a distance (A) of from 1 to 20 mm apart from each other and the projecting height (H) of the folds in unloaded state can likewise be 1 to 20 mm.

According to a preferred embodiment, a plurality of folds can be distributed over the entire width of the absorbent body surface. This results in a maximal product improvement. 5 to 25 folds distributed over the entire width were found to be of particular advantage. Finally, a plurality, preferably 2 to 10 folds, can be provided on a peripheral strip and/or central strip limited to a partial width of the absorbent body surface.

The absorbent article according to the invention is further described with reference to the accompanying drawings.

As is evident from attached FIGS. 14 to 20, the different embodiments of the depicted sanitary napkins exhibit basic structures which correspond to one another in the main points. For example, the backside liquid-impermeable cover sheet is provided in the form of a garment-protecting foil 101 which is disposed under the absorbent body 102 provided as wood pulp fluff pad in the area of the backside 103 thereof, i.e., on the side disposed away from the wearer when the sanitary napkin is applied. The garment-protecting foil 101 further extends with its longitudinal edges 104 around the lateral edge 105 of the absorbent body 102.

A backing sheet 107 which may be, for example, a nonwoven sheet extends with its surface over the frontside surface 106. The backing sheet 107 as well extends with its longitudinal edges 108 around the side edge 105 of the absorbent body 102 and overlaps with the longitudinal edges 104 of the garment-protecting foil 101. In this overlap area these two parts are bonded to each other in conventional manner.

Figure 14:
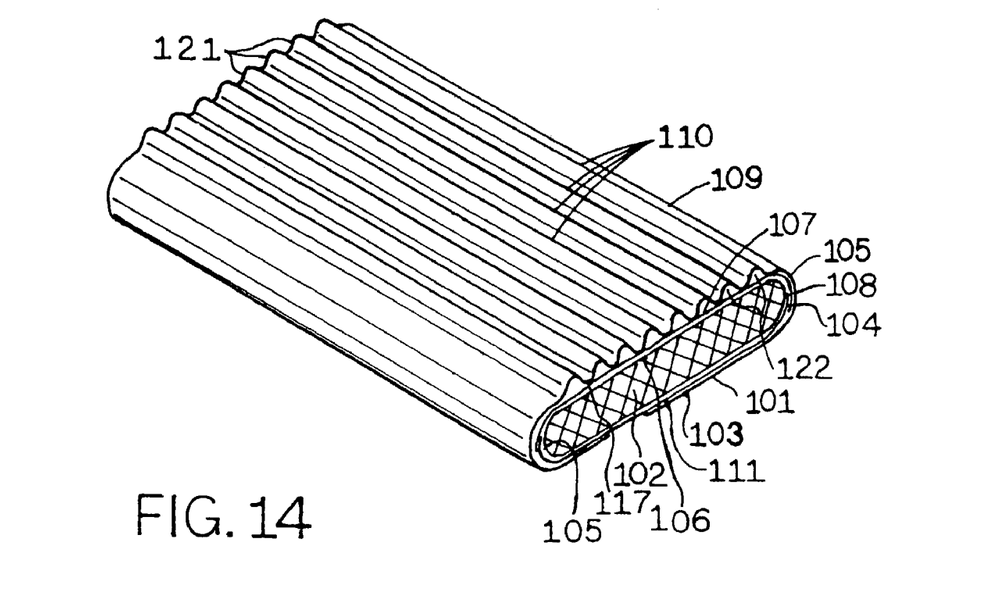
FIGS. 14 to 21 are schematic views of absorbent articles according to the invention.
Figure 15:
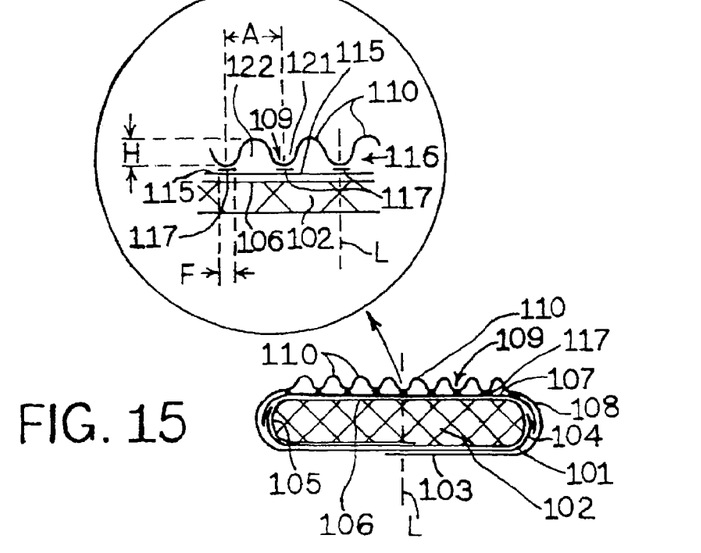
Figure 17:
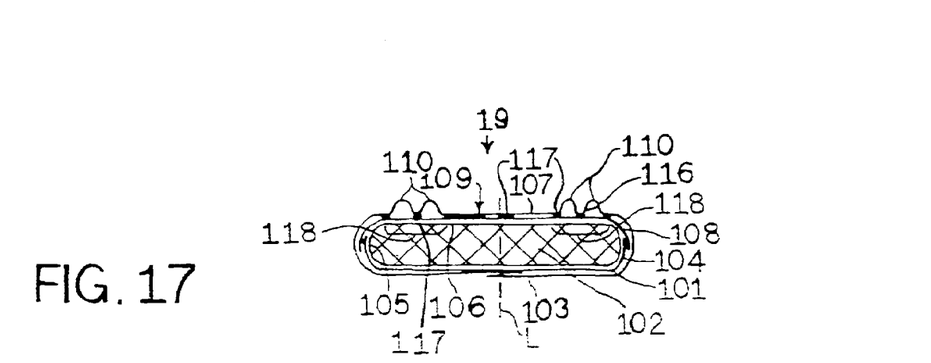

On the backing sheet 107 there is provided a frontside liquid-permeable cover sheet 109 which is provided with folds 110 in a manner which will be described in further detail below. The embodiments of the sanitary napkins shown in FIGS. 14, 15 and 17 are so-called 'fully wrapped sanitary napkins', wherein the cover sheet 109, which may, for example, be formed of a polypropylene carded nonwoven, is wrapped around the absorbent body 102, the backing sheet 107 and the cover sheet 109 on the backside 103 and fixed centrally by an adhesive bond 111.

Figure 16:
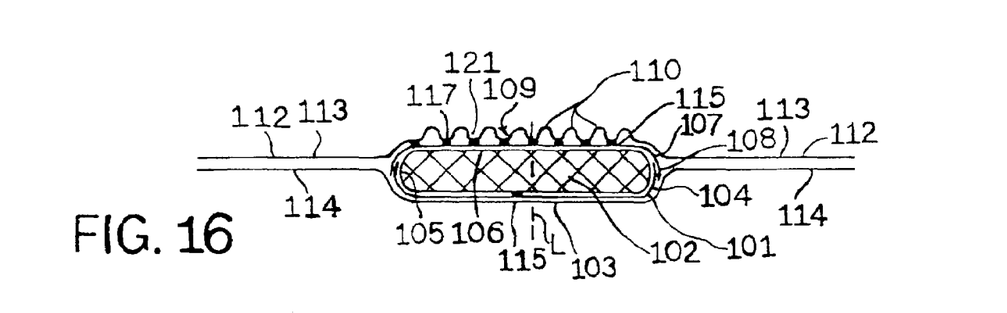
Figure 18:
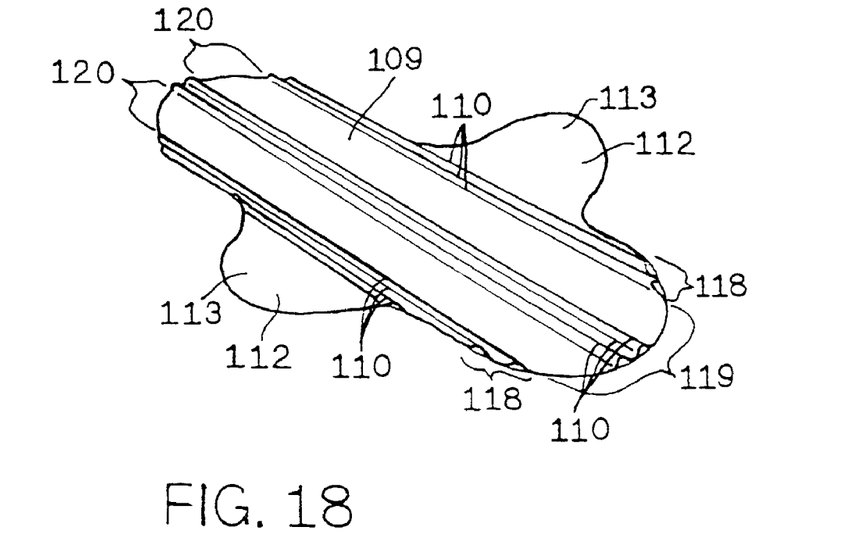

In the embodiments shown in FIGS. 16 and 18, side flaps 112 are provided which are formed by laterally projecting, peripherally bonded flaps 113, 114 of the frontside cover sheet 109 and a backside cover sheet 115, respectively. The cover sheet 115 may be made from nonwoven, as is in particular the case in the embodiment shown in FIG. 16, which comprises a separate garment-protecting foil 101. The garment-protecting foil 101 may also be dispensed with, and the cover sheet can be made of a liquid-impermeable material, for example, polyethylene foil and thus functions as garment-protecting foil.

The different fold configurations used in the various embodiments of the depicted sanitary napkins will now be explained in further detail.

The folds 110 are formed by a suitable folding means in the sanitary napkin manufacturing device such that the valley portions 116 are disposed on the backing sheet 107 in transverse direction of the napkin at a distance A, said distance being in the range between 1 and 20 mm. A distance in the range of from 3 to 5 mm was found to be particularly suitable. The valley portions 116 are fixed to the backing sheet 107 by longitudinally extending adhesive lines 117, which are formed, for example, by a spray adhesive. The folds 110 project upwardly between adjacent valley portions 116, the projecting height H being conceivable to range between 1 and 20 mm. A projection height in the range between 3 and 5 mm was found to be particularly suitable. The valley width F defined by the adhesive lines 117 may be between 0.2 and 10 mm dependent on the distance A and projecting height H. Care must be taken that the valley width F is maximally half of the distance A. At a distance A and a projecting height H of from 3 to 5 mm, valley widths of from 0.5 to 1 mm were found to be useful.

In the embodiments of FIGS. 14 to 16 eight folds 110 are provided which are uniformly distributed over the entire width of the absorbent body surface 102, the fold distance A being about 6 mm.

In the embodiment shown in FIG. 17, two peripheral strips 118 each consisting of two folds 110 extending in longitudinal direction of the sanitary napkin are provided, said folds being provided at a distance A from one another and having a projecting height H of about 6 mm. In the central strips 119 remaining between the two peripheral strips 118 the liquid-permeable cover sheet 109 lies evenly on the backing sheet 107 and is additionally bonded thereto by a central adhesive strip 117. It is also possible to provide a liquid-permeable bond over the entire surface using small amounts of adhesive.

In the sanitary napkin embodiment shown in FIG. 18 there is provided, symmetrically to the central plane L, a further fold configuration with three folds 110 in addition to the folds 110 in the two peripheral strips, with strips 120 without folds remaining between the central folds 110 and the peripheral folds 110.

As is evident from the cross-sections of FIGS. 15 to 17, the grooves 121 between the folds 110 at the outside thereof, on the one hand, and the tubes 122 extending beneath the folds 110 between the bonded valley portions 116, on the other hand, form channels for distributing body fluids in longitudinal direction of the sanitary napkin which are applied to the sanitary napkin.

It should be observed that suitable materials are to be selected for the individual components of the sanitary napkin of the invention from available materials in accordance with the usual criteria commonly applied in the construction of such sanitary materials and appropriate construction measures are to be applied. As to the latter, only by way of example, attention is drawn to the fact that the adhesive strips 117 should be designed such that a sealage of the surface of the backing sheet 107 against liquid penetration is kept at a minimum such that the absorbent surface of the sanitary napkin is kept at a maximum. Accordingly, a spray adhesive may be applied or a meltblown adhesive which is applied in small lines. Laser, ultrasonic or thermal welding or sealing is also conceivable.

Figure 19:
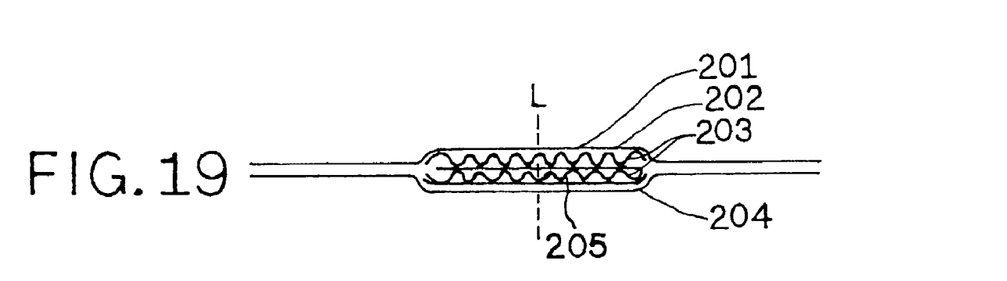
Figure 20:
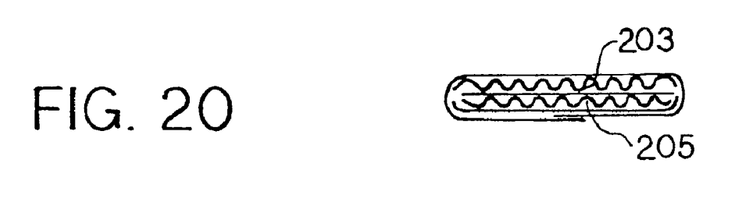

Finally, FIGS. 19 and 20 show embodiments of the absorbent article of the invention wherein the absorbent body 205 is pleated. The articles shown in said Figures, moreover, contain a pleated cover sheet 203 which is bonded with an outer cover sheet 201 at connecting points 202 (FIG. 19). The embodiment shown in FIG. 19 moreover shows a liquid-impermeable cover sheet 204 which is referred to among experts also as "polybaffle".

The absorbent body which comprises at least one corrugated web may comprise, apart from the above-mentioned materials carded nonwoven and spunbonded nonwoven, also an air-laid fibrous web, laminated or the coform material specified further below. Wood pulp/synthetic fiber mixtures are readily capable to absorb liquids up to 25 g/g liquid. In addition to an absorbent web, the absorbent article may also comprise a superabsorber. These superabsorbers have a liquid absorbency of about 1 to 500 g/g physiologic sodium chloride solution. The absorbent capacity for body fluids is about 1 g/g to 80 g/g.

In particular multi-layer laminates of perforated foils and spunbonded nonwovens or multi-layer laminates of perforated foils and carded nonwovens having a basis weight of about 20 to 200 g/m², preferably 30 to 100 g/m², in particular 42 g/m² and/or a thickness of from 0.15 to 4.0 mm, preferably 0.3 to 1.5 mm, in particular 0.5 mm are suitable as liquid-permeable cover materials.

As component of the absorbent are suitable materials of carded nonwoven, a spunbonded nonwoven, web material of a mixture of wood pulp and synthetic fibers (Coform), a compacted air-laid wood pulp web (airlaid material) or an airlaid web of a mixture of wood-pulp and synthetic fibrous web (thermofixed airlaid material). Suitable are furthermore prism and coform materials, absorbent webs of airlaid woodpulp, wood pulp/synthetic fiber mixtures or synthetic fiber webs having a basis weight of from about 12 to 400 g/m², preferably 50 to 150 g/m², in particular 100 g/m² and/or thicknesses of from 0.1 to 3 mm, preferably 0.2 to 2mm, in particular 1 mm.

The bodyside cover sheet should preferably exhibit hydrophilic properties. Possible further transfer sheets and/or materials between the bodyside cover sheet and absorbent body may both be hydrophilic as well as hydrophobic.

It is self-evident for the person skilled in the art, that the pleated cover sheet 203 can also be replaced by a non-pleated sheet. Even if only at least part of the absorbent body is pleated, the lateral leak-proofness of the sanitary article of the invention is increased and an improved longitudinal distribution of the absorbed liquid is achieved. Moreover, it is a matter-of-course that both the liquid-permeable cover sheet and the liquid-impermeable cover sheet of such an absorbent article may be composed of an at least partially corrugated absorbent body made of the materials described in more detail above.

Figure 21:
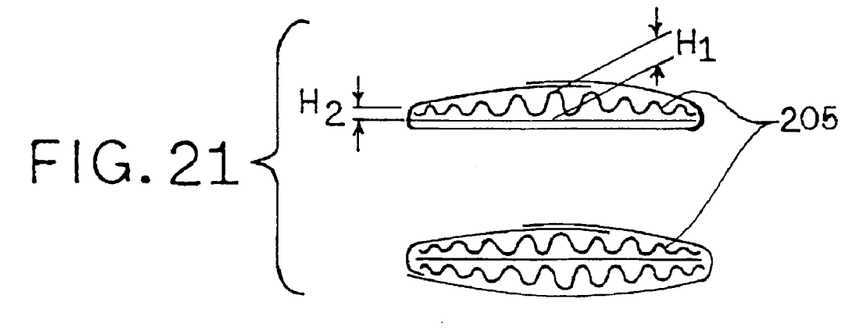

Referring to FIGS. 14 and 21, FIG. 21 shows an embodiment of the absorbent article of the invention wherein the absorbent body 205 is corrugated, and wherein FIG. 21 corresponds to the main points shown in FIG. 14 such as constant heights of the corrugations along the length of the web, the corrugations, as shown in FIG. 21, being of different heights along a direction transverse to the length of the web. The corrugation height $H_1$ in the centre of the absorbent article is preferably maximal ten times higher than the corrugation height $H_2$ in the peripheral portions of the article. Thus, the corrugations may have a graduated height with the height of the corrugations decreasing over the transverse length of the web, as shown for example in FIG. 21.

The longitudinally corrugated webs (pleated webs) produced according to the invention are applied to ultra-thin absorbent bodies. The performance data of corresponding absorbent articles are summarized in Table 2.

The materials specified in Table 2, Prism, Ekotec and Coform have the following properties:

Prism: Special spunbonded nonwoven having a high volume, treated on one side or two sides, basis weights of from about 12 to about 80 g/m². Prism 0.5 corresponds to a basis weight of about 17 g/m², Prism 1.0 corresponds to a basis weight of about 35.0 g/m².

Ekotec: High loft carded nonwoven, dried by hot air (hot through air dried), high volume, basis weight of from about 12 to about 70 g/m².

Coform: wood pulp/polypropylene mixture, fibrilized wood pulp strengthened with spun PP fibers, basis weight of from about 40 to about 400 g/m².

The treatment of Prism on one side or two sides by means of an Arivage method causes an improved liquid absorption and a faster penetration of the liquid, especially if the material is hydrophilized.

TABLE 2

| pleated material | support material | absorbency rate (sec) | amount of rewel (g) | rewel area (cm³) | cover force (%) | longitudinal elongation (mm) | thickness (mm) | compressibility (%) | flexural strength (N) |
|---|---|---|---|---|---|---|---|---|---|
| tool depth: 1.2 mm | | | | | | | | | |
| Sandler carded nonwoven | Prism 0.5 | 2.48 | 0.56 | 8.49 | 20 | 65 | 1.93 | 59 | 0.20 |
| | Prism 1.0 | 2.22 | 0.50 | 7.93 | 18 | 69 | 1.98 | 49 | 0.24 |
| | Ekotec | 2.72 | 0.53 | 7.44 | 17 | 50 | 2.01 | 55 | 0.38 |
| | Coform, 120 g | 3.02 | 0.67 | 10.03 | 16 | | 2.54 | 38 | 1.60 |
| Corosoft spunbonded nonwoven | Prism 0.5 | 2.02 | 0.50 | 7.52 | 16 | | 1.92 | 59 | 0.30 |
| | Prism 1.0 | 1.70 | 0.38 | 8.29 | 16 | 65 | 2.34 | 49 | 0.42 |
| | Ekotec | 2.35 | 0.46 | 6.15 | 17 | | 2.35 | 48 | 0.52 |
| | Coform, 120 g | 3.39 | 0.62 | 9.29 | 18 | | 2.92 | 35 | 1.75 |
| laminate perforated foil/Sandler | Prism 0.5 | 2.26 | | | | | 2.29 | 26 | 1.05 |
| | Prism 1.0 | 2.12 | 0.02 | 0.10 | 31 | | 2.26 | 34 | 1.08 |
| | Ekotec | 4.82 | 0.02 | 0.26 | 40 | | 2.36 | 25 | 1.60 |
| | Conform, 120 g | 7.88 | 0.09 | 0.16 | 36 | | 3.31 | 21 | 2.61 |
| tool depth: 2.5 mm | | | | | | | | | |
| Sandler carded nonwoven | Prism 0.5 | 2.73 | 0.58 | 8.74 | 24 | 80 | 1.97 | 58 | 0.25 |
| | Prism 1.0 | 2.03 | 0.53 | 8.25 | 21 | 59 | 2.36 | 46 | 0.26 |
| | Ekotec | 2.25 | 0.55 | 6.82 | 20 | 43 | 2.15 | 53 | 0.32 |
| | Coform, 120 g | 3.99 | | | | | 2.63 | 38 | 1.64 |
| Corosoft spunbonded nonwoven | Prism, 0.5 | 2.05 | | | | | 2.35 | 60 | 0.32 |
| | Prism 1.0 | 1.98 | 0.48 | 7.51 | 20 | 63 | 2.82 | 55 | 0.37 |
| | Ekotec | 1.70 | | | | | 2.87 | 53 | 0.40 |
| | Coform, 120 g | 2.47 | | | | | 2.95 | 39 | 1.90 |
| laminate perforated foil/Sandler | Prism 0.5 | 3.92 | | | | | 2.43 | 32 | 1.38 |
| | Prism 1.0 | 2.55 | | | | | 3.68 | 49 | 1.41 |
| | Ekotec | 6.00 | | | | | 3.22 | 30 | 2.17 |
| | Conform, 120 g | 9.51 | | | | | 3.44 | 26 | 2.82 |
| laminate perforated foil/Sandler | Prism 0.5 | 2.80 | 0.33 | 4.78 | 27 | 86 | | | |

The invention claimed is:
1. An absorbent article, comprising:
a. a liquid-impermeable cover sheet;
b. a liquid-permeable cover sheet, and
c. an absorbent body between the liquid-impermeable cover sheet and the liquid-permeable cover sheet, wherein said liquid-permeable cover sheet and said absorbent body each comprise a corrugated web having grooves and corresponding ridges, said corrugated webs extendable by at least 10 percent in a direction transverse to the grooves and ridges, and corrugations within said corrugated webs have a graduated height.

2. An absorbent article as in claim 1 wherein said absorbent body comprises absorbent material in addition to the corrugated webs.

3. An absorbent article as in claim 1 wherein said absorbent body comprises a mixture of wood pulp and synthetic fiber.

4. An absorbent article as in claim 1 wherein said absorbent body comprises a compacted air-laid wood pulp web.

5. An absorbent article as in claim 1 wherein said absorbent body has a basis weight of about 12 to 400 g/m².

6. An absorbent article as in claim 1 wherein said absorbent body has a basis weight of 50 to 150 g/m².

7. An absorbent article as in claim 1 wherein said absorbent body has a basis weight of 100 g/m².

8. An absorbent article as in claim 1 wherein said absorbent body has a thickness of 0.1 to 3 mm.

9. An absorbent article as in claim 1 wherein said absorbent body has a thickness of 0.2 to 2 mm.

10. An absorbent article as in claim 1 wherein said absorbent body has a thickness of 1 mm.

11. An absorbent article as in claim 1 wherein said absorbent body is made from at least one of a carded nonwoven, a spunbonded nonwoven, a multiple layer laminate of perforated foil and spunbonded nonwoven, and a multiple layer laminate of perforated foil and carded woven.

12. An absorbent article as in claim 11 wherein at least one of said carded nonwoven and said spunbonded nonwoven comprises a basis weight of 6 to 80 g/m².

13. An absorbent article as in claim 11 wherein at least one of said carded nonwoven and said spunbonded nonwoven comprises a basis weight of 10 to 30 g/m².

14. An absorbent article as in claim 11 wherein at least one of said carded nonwoven and said spunbonded nonwoven comprises a basis weight of 16 to 18 g/m².

15. An absorbent article as in claim 11 wherein at least one of said carded nonwoven and said spunbonded nonwoven comprises a thickness of 0.05 to 1.5 mm.

16. An absorbent article, comprising:
a. a liquid-impermeable cover sheet,
b. a liquid-permeable cover sheet, and
c. an absorbent body between the liquid-impermeable cover sheet and the liquid-permeable cover sheet, wherein said liquid-permeable cover sheet and said absorbent body each comprise a corrugated web, said corrugated webs are drawn in by a value of at least 1.32, and corrugations within said corrugated webs have a graduated height.

17. An absorbent article as in claim 16 wherein said absorbent body comprises a mixture of wood pulp and synthetic fiber.

18. An absorbent article as in claim 16 wherein said absorbent body comprises a compacted air-laid wood pulp web.

19. An absorbent article as in claim 16 wherein said absorbent body has a basis weight of about 12 to 400 g/m².

20. An absorbent article as in claim 16 wherein said absorbent body has a basis weight of 50 to 150 g/m².

21. An absorbent article, comprising:
a. a liquid-impermeable cover sheet,
b. a liquid-permeable cover sheet, and
c. an absorbent body between the liquid-impermeable cover sheet and the liquid-permeable cover sheet, wherein said liquid-permeable cover sheet, said liquid impermeable cover sheet, and said absorbent body each comprise a corrugated web wherein corrugations within said corrugated webs have different heights (H1) when compared to each other.

22. An absorbent article as in claim 21 wherein said absorbent body comprises a mixture of wood pulp and synthetic fiber.

23. An absorbent article as in claim 21 wherein said absorbent body comprises a compacted air-laid wood pulp web.

24. An absorbent article as in claim 21 wherein said absorbent body has a basis weight of about 12 to 400 g/m².

25. An absorbent article as in claim 21 wherein said absorbent body has a basis weight of 50 to 150 g/m².

26. An absorbent article as in claim 21 wherein the corrugation height (H1) of corrugations in the center of said absorbent article are higher than the corrugation height of corrugations in peripheral portions of the absorbent article.

27. An absorbent article as in claim 21 wherein the corrugation height (H1) of corrugations in said corrugated webs are graduated downwardly from centrally located ones of said corrugations.

28. An absorbent article as in claim 21 wherein said liquid impermeable cover sheet, said permeable cover sheet, and said absorbent body each comprise a corrugated web wherein corrugations therein have constant heights (H1) along a length of the webs and different heights (H2) when compared to each other along a direction transverse to the length of the webs.

* * * * *